United States Patent [19]
Odawara

[11] Patent Number: 5,935,834
[45] Date of Patent: Aug. 10, 1999

[54] REVERSE TRANSCRIPTASE COMPOSITION HAVING IMPROVED STORAGE STABILITY

[75] Inventor: Fumitomo Odawara, Shizuoka, Japan

[73] Assignee: Asahi Kasei Kogyo Kabushiki Kaisha, Osaka, Japan

[21] Appl. No.: 08/836,380

[22] PCT Filed: Nov. 10, 1995

[86] PCT No.: PCT/JP95/02304

§ 371 Date: May 7, 1997

§ 102(e) Date: May 7, 1997

[87] PCT Pub. No.: WO96/15235

PCT Pub. Date: May 23, 1996

[30] Foreign Application Priority Data

Nov. 11, 1994 [JP] Japan .................................. 6-277618

[51] Int. Cl.⁶ .............................. C12N 9/12; C12N 9/10; C12N 9/96; C12P 19/34
[52] U.S. Cl. ......................... 435/194; 435/188; 435/193; 435/91.2
[58] Field of Search .................... 435/188, 193, 435/194, 91.2

[56] References Cited

U.S. PATENT DOCUMENTS

| | | | |
|---|---|---|---|
| 4,868,115 | 9/1989 | Obayashi et al. | 435/188 |
| 5,554,498 | 9/1996 | Filler et al. | 435/5 |
| 5,556,771 | 9/1996 | Shen et al. | 435/91.2 |
| 5,599,660 | 2/1997 | Ramanujam et al. | 435/4 |
| 5,614,387 | 3/1997 | Shen et al. | 435/91.2 |

FOREIGN PATENT DOCUMENTS

92/08800  5/1992  WIPO .

OTHER PUBLICATIONS

G.L. Rowley, et al., "Stabilization and Activation of Recombinant Human Immunodeficiency Virus–1 Reverse Transcriptase–P66", pp. 673–679, Biochemical and Biophysical Research Communication, Vol. 167, No. 2, Mar. 16, 1990.

*Primary Examiner*—Jon P. Weber
*Attorney, Agent, or Firm*—Young & Thompson

[57] ABSTRACT

Disclosed is a reverse transcriptase composition having improved storage stability, comprising a reverse transcriptase, an effective stabilizing amount of at least one organic stabilizing reagent selected from trehalose and a nucleic acid containing a transcriptional initiation site recognizable by the enzyme, and an effective stabilizing amount of a metal salt capable of producing bivalent positive ions in an aqueous solution of the metal salt. Also disclosed is a method for improving storage stability of a reverse transcriptase, which comprises adding the above-mentioned organic stabilizing reagent and metal salt to a reverse transcriptase. The composition of the present invention can be stably stored for a prolonged period of time at a temperature up to at least 4° C. Further, by virtue of a relatively high temperature usable for stable storage, the viscosity of the composition can be advantageously maintained at a low level, so that it becomes possible to accurately dispense the composition by a quantity corresponding to a desired enzyme activity, thereby achieving high reproducibility in experiments using the reverse transcriptase. Therefore, in the determination of a virus, in which a reverse transcriptase activity is used as an index, the composition of the present invention can be advantageously used as a standard substance for determining the amount of virus.

17 Claims, No Drawings

REVERSE TRANSCRIPTASE COMPOSITION HAVING IMPROVED STORAGE STABILITY

BACKGROUND OF THE INVENTION

1. Field of the Invention

The present invention relates to a novel reverse transcriptase composition having improved storage stability. More particularly, the present invention is concerned with a reverse transcriptase composition having improved storage stability, comprising a reverse transcriptase, an effective stabilizing amount of at least one organic stabilizing reagent selected from the group consisting of trehalose and a nucleic acid containing a transcriptional initiation site recognizable by the reverse transcriptase, and an effective stabilizing amount of a metal salt capable of producing bivalent positive ions in an aqueous solution of the metal salt. The present invention is also concerned with a method for improving storage stability of a reverse transcriptase, which comprises adding to a reverse transcriptase an effective stabilizing amount of at least one organic stabilizing reagent selected from the group consisting of trehalose and a nucleic acid containing a transcriptional initiation site recognizable by the reverse transcriptase, and an effective stabilizing amount of a metal salt capable of producing bivalent positive ions in an aqueous solution of the metal salt.

Conventionally, for maintaining the stability of a reverse transcriptase, it has been necessary to store the reverse transcriptase at a temperature as low as −20 to −80° C. According to the present invention, however, a reverse transcriptase can be stably stored in the form of the above-mentioned composition for a prolonged period of time at a temperature up to at least 4° C. without suffering denaturation of the reverse transcriptase. Further, by virtue of such a relatively high temperature usable for stable storage, the viscosity of the reverse transcriptase composition of the present invention can be advantageously maintained at a low level, so that it becomes possible to accurately dispense the composition by a quantity corresponding to a desired enzyme activity, thereby achieving high reproducibility in experiments using the reverse transcriptase.

The reverse transcriptase composition of the present invention, which has improved storage stability, can be advantageously used in the fields of genetic engineering and virology, with respect to various techniques in which the reverse transcriptases are employed. Particularly, in a method generally employed for the determination of a virus, in which a reverse transcriptase activity is used as an index, the transcriptase composition of the present invention can be advantageously used as a standard substance for determining the amount of virus.

2. Prior Art

Reverse transcriptase is an enzyme having the activity of synthesizing from an RNA template a DNA having a nucleotide sequence complementary to the RNA. This enzyme was discovered in the recent development of molecular biology. Examples of reverse transcriptases include those which are derived from avian myeloblast virus (AMV), Ras associated virus type 2 (RAV-2), mouse molony murine leukemia virus (M-MuLV) and human immunodefficiency virus type 1 (HIV-1). These reverse transcriptases are commercially readily available.

Further, on a laboratory scale, a reverse transcriptase can be easily obtained by directly separating the enzyme from a virus. For example, a reverse transcriptase can be easily prepared by treating particles of retroviruses, such as human immunodefficiency virus Type 2 (HIV-2), human T-cell leukemia virus type 1 (HTLV-1), simian AIDS virus (SIV), feline AIDS virus (FIV) and Rous related avian sarcoma virus, with a surfactant, such as Triton X-100 (manufactured and sold by Sigma Chemical Company, USA). The above-mentioned reverse transcriptases have been widely used in the synthesis of a cDNA from a messenger RNA.

Reverse transcriptase is also used in the PCR (polymerase chain reaction) method which is recently a most widely used nucleic acid amplification technique. Specifically, the PCR method is a technique to amplify at least one type of nucleic acid using a thermostable DNA polymerase and two types of primers specific to the nucleic acid, in which a cycle of DNA polymerase reaction and annealing is repeatedly performed by repeating the cycle of raising and lowering of the temperature of the reaction system. In the PCR method, the activity of the DNA polymerase is specific to the DNA. Therefore, when an RNA is used as a starting material for the nucleic acid amplification using the technique of the PCR method, it is necessary to employ a method in which a DNA is prepared from the RNA using a reverse transcriptase, and the obtained DNA is amplified by the PCR method [such a method is called an "RT-PCR (reverse transcription polymerase chain reaction) method"]. For this reason, in the study of an RNA using the technique of the PCR method, the reverse transcriptase is indispensable. Particularly, in recent years, the number of studies made with respect to the determination of the amount of a virus, such as HIV, HCV or the like, in terms of the RNA amount has been increasing, so that the number of the test kits developed for use in such determination has also been increasing. Therefore, the reverse transcriptase is a commercially important enzyme.

Further, the reverse transcriptase is also employed in the LCR (ligase chain reaction) method which is another nucleic acid amplifying technique. Specifically, in the LCR method, the amplification of at least one type of nucleic acid is performed in substantially the same manner as in the PCR method, except that a thermostable DNA ligase is used instead of the thermo-stable DNA polymerase, in which the cycle of ligation reaction and annealing is repeatedly performed by repeating the cycle of raising and lowering of the temperature of the reaction system. In the LCR method also, the activity of the DNA ligase is specific to the DNA. Therefore, when an RNA is used as a starting material for the nucleic acid amplification using the technique of the LCR method, it is necessary to employ a method in which a DNA is prepared from the RNA using a reverse transcriptase, and the obtained DNA is amplified by the LCR method [such a method is called an "RT-LCR (reverse transcription ligase chain reaction) method"]. For this reason, also in the study of an RNA using the technique of the LCR method, the reverse transcriptase is indispensable.

The reverse transcriptase is also used in NASBA (nucleic acid sequence based amplification) method. Specifically, the NASBA method is a method of amplifying a nucleic acid by using a reverse transcriptase, a DNA polymerase, a RNase H and two types of primers, in which the amplification of the nucleic acid is performed at room temperature by the cascade reaction of the enzymes. In this method also, the reverse transcriptase is indispensable for amplifying a nucleic acid.

On the other hand, in the field of virology, it has generally been practiced to determine the amount of virus from the activity of a reverse transcriptase contained in the virus, in which a reverse transcriptase is used as a standard substance. Examples of reverse transcriptases used in this field include those which are derived from retroviruses, such as human immunodefficiency virus type 1 (HIV-1), human immunodefficiency virus type 2 (HIV-2), human T-cell leukemia virus type 1 (HTLV-1), simian AIDS virus (SIV), feline AIDS virus (FIV) and Rous avian sarcoma virus.

These reverse transcriptases are generally stored at a temperature of from −20 to −80° C. in the form of a solution thereof in a buffer comprising a monovalent or divalent metal salt (such as NaCl or $MgCl_2$), an SH group-containing protective reagent (such as mercaptoethanol and/or dithiothreitol) and a high concentration (about 50% by volume) of glycerol.

Conventionally, for performing the reverse transcription reaction which is usually conducted at 37° C., the preparatory operation prior to the reaction is generally conducted as follows. A container containing the reverse transcriptase is taken out from a freezer having a temperature as low as −20 to −80° C. and placed under ambient temperature conditions of 4° C. or more (the reverse transcriptase is unstable under such temperature conditions), followed by taking out a necessary amount of the reverse transcriptase from the container by dispensing. Then, the container is returned to the freezer having a temperature of from −20 to −80° C. In this preparatory operation, the reverse transcriptase is necessarily left under the above-mentioned temperature conditions, at which the enzyme is unstable, for a prolonged period of time during the handling thereof. Therefore, as the number of such operations increases, the activity of the stored reverse transcriptase remaining in the container decreases. Therefore, it is difficult to maintain the activity of the reverse transcriptase at the same level for a prolonged period of time. For avoiding the lowering of the activity of the reverse transcriptase, which is caused by the repetition of the above operation, it has conventionally been practiced to conduct the operation of taking out the necessary amount of the solution containing the reverse transcriptase from the container within a short period of time inside of the freezer (having a temperature of from −20 to −80° C.), followed by performing a reverse transcription reaction using the reverse transcriptase immediately after the above removing operation. However, in this technique, the temperature of the removed solution containing the reverse transcriptase is inevitably very low, so that the solution has high viscosity. Therefore, with this method, it is impossible to accurately dispense the solution in a quantity corresponding to a desired reverse transcriptase activity. Further, each of the above-mentioned conventional techniques is accompanied by the problem of a bad smell caused by the SH group-containing protective reagent used as a stabilizer (e.g., mercaptoethanol), which has an unfavorable influence on the person conducting the operation.

Further, with respect to the technique to stabilize the reverse transcriptase, a stabilizing method for the reverse transcriptase using a hybridization product of a template-primer represented by $(rA)_n(dT)_{12-18}$ is known [(see Biochemical and Biophysical Research Communication Vol 167, (2), pp 673 (1990)]. However, in this method, the enzyme activity retaining ratio as measured after the enzyme is stored at 4° C. for 300 hours is as low as 70%, so that satisfactory storage stability cannot be achieved by this method.

As can be seen from the above, in experimental studies using the reverse transcriptase, it has conventionally been difficult to conduct experiments with high reproducibility, due to the instability of the reverse transcriptase.

Due to a recent sudden increase in the number of patients infected with HIV, there has been a rapid increase in the number of testings for measuring the reverse transcriptase activity which is used for determining the amount of virus. In the testings, the reverse transcriptase is used as a standard substance. However, it has conventionally been difficult to measure the reverse transcriptase activity with respect to many samples with high reproducibility, due to the instability of the reverse transcriptase. Especially when molecular biological experiments using a reverse transcriptase must be conducted for a long period of time, various disadvantages are likely to occur. That is, during the repetition of the operation of taking out the reverse transcriptase from a container stored in a freezer or the like and returning the container to the freezer or the like, the reverse transcriptase remaining in the container is caused to be denaturated. Therefore, since such a remaining denaturated enzyme can no longer be used, it becomes necessary to replace the denaturated enzyme with a newly purchased or newly prepared reverse transcriptase to continue the experiments. This is disadvantageous from the viewpoint of energy, cost and time.

For improving the storage stability of the reverse transcriptase, it has been proposed to use the reverse transcriptase in a freeze-dried form which is more stable than in an aqueous solution form. However, in the conventional storage technique for the reverse transcriptase, a reverse transcriptase solution for storage contains glycerol in a high concentration. Therefore, due to the high concentration of glycerol in the solution for storage, it is difficult to obtain the reverse transcriptase in a freeze-dried form, so that the stability of the reverse transcriptase for a prolonged period of time has been unable to be realized.

If the stability of the reverse transcriptase can be successfully improved such that the storage stability of the reverse transcriptase at a temperature up to at least 4° C. can be maintained for a prolonged period of time, it would become unnecessary to use a freezer specially designed for storing the reverse transcriptase at a temperature as low as −20 to −80° C. It would lead to a possibility of reduction in the cost for the above-mentioned virological studies and experiments.

Further, if the above-mentioned improved storage stability is achieved, it would become possible to lower the viscosity of the solution containing the reverse transcriptase, so that it would become possible to accurately dispense the composition by a quantity corresponding to a desired enzyme activity, thereby achieving high reproducibility in experiments using the reverse transcriptase. The achievement of such an improved storage stability of the reverse transcriptase is advantageous especially when the reverse transcriptase is used as a standard substance in the determination of the amount of virus, in which the reverse transcriptase activity is used as an index. Further, by virtue of the high reproducibility of experiments using a reverse transcriptase, it becomes possible to analyze a large number of samples by the use of a reverse transcriptase. This is advantageous in view of the recent tendency that the numbers of the samples to be analyzed by the use of a reverse transcriptase is increasing.

Therefore, in various techniques using a reverse transcriptase, it has been strongly desired to improve the storage stability of a reverse transcriptase, so that experiments using a reverse transcriptase can be conducted with high reproducibility and at low cost.

SUMMARY OF THE INVENTION

The present inventors have made extensive and intensive studies with a view toward solving the abovementioned problems. As a result, it has unexpectedly been found that a reverse transcriptase composition obtained by adding to a reverse transcriptase at least one organic stabilizing reagent selected from the group consisting of trehalose and a nucleic acid containing a transcriptional initiation site recognizable by the reverse transcriptase, and a metal salt capable of producing bivalent positive ions in an aqueous solution of the metal salt, exhibits excellent stability even at a temperature up to at least 4° C. The present invention has been completed, based on the above novel findings.

Accordingly, it is an object of the present invention to provide a reverse transcriptase composition which can maintain the enzyme activity thereof for a prolonged period of time even under relatively high temperature conditions as compared to the conventionally employed storage temperature conditions, so that not only is the use of this composition economically advantageous, but the composition can also be advantageously used to obtain experimental data with high reproducibility.

It is another object of the present invention to provide a method for improving the storage stability of a reverse transcriptase so that the above-mentioned excellent effects can be achieved.

The foregoing and other objects, features and advantages of the present invention will be apparent from the following detailed description and appended claims.

DETAILED DESCRIPTION OF THE INVENTION

In one aspect of the present invention, there is provided a reverse transcriptase composition having improved storage stability, comprising a reverse transcriptase, an effective stabilizing amount of at least one organic stabilizing reagent selected from the group consisting of trehalose and a nucleic acid containing a transcriptional initiation site recognizable by the reverse transcriptase, and an effective stabilizing amount of a metal salt capable of producing bivalent positive ions in an aqueous solution of the metal salt.

In another aspect of the present invention, there is provided a method for improving storage stability of a reverse transcriptase, which comprises adding to a reverse transcriptase an effective stabilizing amount of at least one organic stabilizing reagent selected from the group consisting of trehalose and a nucleic acid containing a transcriptional initiation site recognizable by the reverse transcriptase, and an effective stabilizing amount of a metal salt capable of producing bivalent positive ions in an aqueous solution of the metal salt.

With respect to the reverse transcriptase used in the present invention, there is no particular limitation, as long as it is an enzyme derived from a retrovirus or the like, and has the enzyme activity of synthesizing a cDNA from an RNA template. As examples of reverse transcriptases which are commercially readily available, there can be mentioned reverse transcriptases which are derived from avian myeloblast virus, Ras associated virus type 2, mouse molony murine leukemia virus and human immunodefficiency virus type 1. Further, the reverse transcriptase used in the present invention can be obtained by treating particles of retroviruses, such as human immunodefficiency virus type 1, human immunodefficiency virus type 2, human T-cell leukemia virus, simian AIDS virus, feline AIDS virus and Rous related avian sarcoma virus, with a surfactant, such as Triton X-100. In this case, if desired, the obtained reverse transcriptase may be purified.

In the present invention, it is preferred that the reverse transcriptase is one derived from human immunodefficiency virus, which is commercially available and most widely used. With respect to the concentration of the reverse transcriptase in the composition of the present invention, there is no particular limitation. For example, the concentration may be in the range of from 0.01 mU/$\mu$l to 10 U/$\mu$l. In the present invention, the enzyme activity is expressed using a unit "U", wherein 1 U corresponds to the enzyme activity to incorporate 10 nmol of nucleotides in the form of a DNA synthesized by a reverse transcription reaction preformed using oligodeoxythymine nucleotide (oligo dT)·polyadenine ribonucleotide (poly A) (a hybridization product of a primer and a template RNA), a reverse transcriptase and mononucleotides under reaction conditions wherein the reaction temperature is 37° C., the pH of the reaction system is 7.4, and the reaction time is 30 minutes.

In the present invention, it is preferred that the above-mentioned organic stabilizing reagent comprises trehalose and a nucleic acid containing a transcriptional initiation site recognizable by the reverse transcriptase.

With respect to the trehalose used as the organic stabilizing agent in the present invention, it is preferred that the trehalose is used in an amount of from 30 to $3.1 \times 10^{11}$ molecules, more preferably from 31 to $3.09 \times 10^{11}$ molecules, most preferably from 3000 to $3.09 \times 10^{11}$ molecules, per molecule of the reverse transcriptase. Alternatively, trehalose may be used in an amount of from 0.01 to 50% by weight, based on the weight of the reverse transcriptase composition.

With respect to the nucleic acid used as the organic stabilizing agent in the present invention, which contains a transcriptional initiation site recognizable by the reverse transcriptase, it is preferred that the nucleic acid is a hybridization product of a template RNA and a primer DNA. With respect to the hybridazation product, there is no particular limitation, as long as the template RNA of the hybridization product has a region protruding outwardly of a position of the template RNA, which position corresponds to the 3'-terminus of the primer DNA. The length of the above-mentioned protruding region of the template RNA is not particularly limited. In the present invention, as the hybridization product of the primer DNA and the template RNA (template-primer), it is preferred to use at least one hybridization product selected from the group consisting of a hybridization product of a template RNA composed essentially of adenine ribonucleotide and a primer composed essentially of oligodeoxythymine nucleotide, a hybridization product of a template RNA composed essentially of uracil ribonucleotide and a primer composed essentially of oligodeoxyadenine nucleotide, a hybridization product of a template RNA composed essentially of cytosine ribonucleotide and a primer composed essentially of oligodeoxyguanine nucleotide, and a hybridization product of a template RNA composed essentially of guanine ribonucleotide and a primer composed essentially of oligodeoxycytosine nucleotide. Specific examples of hybridazation products include oligo dT·poly A, oligo dA·poly U, oligo dC·poly G and oligo dG·poly C. Of these hybridazation products, oligo dT·poly A is especially preferred. With respect to the length of the molecular chain of each of the above-mentioned nucleotides, there is no particular limitation, as long as the length is sufficient for the reverse transcriptase to recognize the initiation site for reverse transcription. With respect to the above-mentioned hybridization product, it is preferred that the primer region thereof, in which the primer DNA is bonded to the template RNA so as to form a double strand structure, has a length corresponding to 5 nucleotides or more. Alternatively, the reverse transcriptase composition of the present invention may separately contain a single strand RNA and a single strand DNA, which can be hybridized with each other before use of the reverse transcriptase composition.

In the reverse transcriptase composition of the present invention, it is preferred that the amount of the nucleic acid containing a transcriptional initiation site recognizable by the reverse transcriptase is in the range of from 250 to $6 \times 10^{12}$ molecules, more preferably from 2.64 to $5.28 \times 10^{12}$ molecules, most preferably from $2.64 \times 10^{5}$ to $2.64 \times 10^{12}$ molecules, relative to $10^6$ molecules of the reverse transcriptase.

With respect to the metal salts capable of producing bivalent positive ions in an aqueous solution, examples thereof include salts of bivalent metals, such as magnesium (Mg), manganese (Mn), calcium (Ca), zinc (Zn), cadmium (Cd) and copper (Cu). Specific examples of bivalent metal salts include $MgCl_2$, $MnCl_2$, $CaCl_2$, $ZnCl_2$, $CdCl_2$, $CuCl_2$, $MgSO_4$, $MnSO_4$, $CdSO_4$ and $CuSO_4$. Of these metal salts, $MgCl_2$, $MnCl_2$, $CaCl_2$ and $MgSO_4$ are preferred. In the reverse transcriptase composition of the present invention, it is preferred that the amount of the metal salt is in the range of from 100 to $1.2 \times 10^{13}$ molecules, more preferably from 117 to $1.17 \times 10^{13}$ molecules, most preferably from $1.17 \times 10^{3}$ to $2.34 \times 10^{12}$ molecules, relative to 100 molecules of the reverse transcriptase. Alternatively, the amount of the metal salt may be in the range of from 0.01 to 500 mM, preferably from 0.1 to 100 mM, per mole of the reverse transcriptase composition. These metal salts can be used individually or in combination.

In the present invention, if desired, an SH group-containg protective reagent, such as mercaptoethanol, dithiothreitol, dithioerythritol or reduced glutathione, may be added to the reverse transcriptase composition. Further, in the present invention, it is preferred that the pH of the reverse transcriptase composition is adjusted to an optimal pH for stabilizing the reverse transcriptase by the use of an appropriate buffer, such as a Tris buffer, a phosphate buffer, an acetic acid buffer, and a Good's buffer. In the present invention, it is preferred that the pH of the reverse transcriptase composition is in the range of from 5 to 10, more preferably from 6 to 9. Further, a salt, such as NaCl and KCl, may be added to the composition of the present invention. In the present invention, depending on the type of the materials used for a container for accommodating the reverse transcriptase composition therein, a protein (such as albumin and IgG), an amino acid or a polyamino acid (such as lysine and poly-L-lysine) and a surfactant may be added to the composition as an adsorption preventive agent for preventing the components of the reverse transcriptase composition from adsorbing to the inner wall of the container. Examples of materials used for the container include plastics, such as polystyrene, polypropylene, Teflon, polyethylene, methylpentene resin (TPX), fluororesin, acrylic resin, polycarbonate, polyurethane and vinyl chloride resin; metals, such as stainless steel, aluminum and titanium; a glass; and a rubber.

When it is intended to obtain the composition of the present invention in the form of a solution thereof, the solution of the composition may be produced either by a method in which the component materials for the composition of the present invention (i.e., trehalose, a nucleic acid containing a transcriptional initiation site recognizable by the reverse transcriptase, a metal salt capable of producing bivalent positive ions in an aqueous solution of the metal salt and, optionally, the above-mentioned various additives) are separately added to a solvent, or a method in which at least two component materials are mixed in advance, and the resultant mixture is added to a solvent (the remaining component materials are added to the solvent separately or in the form of a mixture of at least two component materials). For example, a solution of the reverse transcriptase composition can be prepared by adding a buffer solution containing magnesium chloride, trehalose and, optionally, oligo dT·poly A (as a buffer, any of the above-mentioned buffers can be used) to a solution of the reverse transcriptase.

That is, in the present invention, it is possible to obtain an aqueous solution of the reverse transcriptase composition having improved storage stability, wherein each of the reverse transcriptase, at least one organic stabilizing reagent and the metal salt is contained in the form of an aqueous solution thereof.

The aqueous solution of the composition of the present invention can maintain the improved storage stability for a prolonged period of time. However, when it is desired to enhance the effect of maintaining the improved storage stability of the composition for a prolonged period of time, the aqueous solution of the composition may be subjected to freeze-drying to obtain the composition of the present invention in a freeze-dried form. The freeze-dried product of the composition of the present invention can be prepared by a method in which the solution of the reverse transcriptase composition (which is used as a mother liquor for the freeze-dried product) is prepared by mixing a buffer solution containing trehalose (used in an amount such that the mother liquor has a trehalose concentration of from 0.01 to 50% by weight), a template-primer (used in an amount of from $264 \times 10^{-4}$ to $5.28 \times 10^{12}$ molecules, relative to $10^6$ molecules of the of reverse transcriptase) and a metal salt capable of producing bivalent positive ions in an aqueous solution (used in an amount such that the mother liquor has a metal salt concentration of from 0.01 to 500 mM) with an aqueous solution of the reverse transcriptase, and the resultant mixed solution is subjected to freeze-drying to obtain the reverse transcriptase composition in a freeze-dried form. It is preferred that the pH of the above-mentioned mother liquor is adjusted to an optimum pH for stabilizing the reverse transcriptase. If desired, the above-mentioned additives (such as an SH group-containing protective reagent, salts and an adsorption preventive reagent) may be added to the mother liquor.

By the above-mentioned reverse transcriptase composition of the present invention, which has improved storage stability, and the method of the present invention for improving the storage stability of the reverse transcriptase composition, it has become possible to stably store the reverse transcriptase in the form of the above-mentioned composition for a prolonged period of time at a temperature up to at least 4° C., thereby achieving reduction in energy and cost required in various conventional techniques using the reverse transcriptase. Further, by virtue of such a relatively high temperature usable for the storage, the viscosity of the reverse transcriptase composition of the present invention can be advantageously maintained at a low level, so that it becomes possible to accurately dispense the composition by a quantity corresponding to a desired enzyme activity, thereby achieving high reproducibility in experiments using the reverse transcriptase.

BEST MODE FOR CARRYING OUT THE INVENTION

Hereinbelow, the present invention will be described in more detail with reference to the following Examples and Reference Example, but they should not be construed as limiting the scope of the present invention.

In the following Examples and Reference Example, the reverse transcriptase activity was evaluated in accordance with the method of Nakano et al. described in "Kansenshougaku Zashi (The Japanese Journal for Infectious Diseases), vol.68, No. 7, 923–931 (1994), Japan".

EXAMPLE 1

In ten glass vials were individually prepared ten different types of solutions which respectively contained magnesium chloride (manufactured and sold by WAKO PURE CHEMICAL INDUSTRIES LTD., Japan) in concentrations of 0, 0.5, 1, 2, 5, 10, 20, 50, 100 and 200 mM and each of which contained 0.1 M of HEPES (N-2-hydroxyethylpiperazine-N'-2-ethanesulfonic acid) (manufactured and sold by DOJINDO LABORATORIES, Japan; pH 7.8), 0.1% of Triton X-100 (manufactured and sold by Sigma Chemical Company, USA), 0.15% of bovine serum albumin (manufactured and sold by Sigma Chemical Company, USA), 1 mU/$\mu$l of HIV-1 reverse transcriptase (specific activity: 10000 U/mg to 20000 U/mg; molecular weight: 117 Kd) (manufactured and sold by SEIKAGAKU KOGYO CO., LTD., Japan) and 20 $\mu$g/ml of oligo $dT_{12\text{-}18}$·poly A (average molecular weight: 88600; the average number of nucleotides constituting the oligo dT is 12 to 18) (manufactured and sold by Pharmacia Fine Chemicals AB, Sweden). Another set of ten types of solutions having different magnesium chloride concentrations was prepared in the same manner as described above. Thus, there were obtained two sets of sample solutions. The thus obtained two sets of sample solutions were stored for 7 days at 4° C. and at 37° C., respectively. After the storage at the respective temperatures, each of the sample solutions was individually diluted using 0.1% Triton X-100, so that each of the sample solutions contained 0.4 mU/ml of the reverse transcriptase, thereby obtaining test samples. The reverse transcriptase activity of each of the obtained test samples was evaluated by the above-mentioned evaluation method.

On the other hand, two control solutions were prepared in substantially the same manner as described above, except that oligo $dTR_{12\text{-}18}$·poly A and magnesium chloride were not added. Storage of the prepared two control solutions at the respective temperatures, and dilution of the control solutions with 0.1% Triton X-100 performed in the same manner as described above, to thereby obtain two control test samples. The reverse transcriptase activity of each of the obtained two control test samples was evaluated by the above-mentioned evaluation method.

The results are shown in Table 1.

TABLE 1

| Concentration of Magnesium Chloride | Reverse Transcriptase Activity (Absorbance at 405 nm) | |
|---|---|---|
| | 4° C. | 37° C. |
| 0 (Comparative Example | 1.28 | 0.452 |
| 0.5 | 1.32 | 1.008 |
| 1 | 1.346 | 0.806 |
| 2 | 1.222 | 0.745 |
| 5 | 1.202 | 0.871 |
| 10 | 1.442 | 0.97 |
| 20 | 1.332 | 1.235 |
| 50 | 1.152 | 0.607 |

TABLE 1-continued

| Concentration of Magnesium Chloride | Reverse Transcriptase Activity (Absorbance at 405 nm) | |
|---|---|---|
| | 4° C. | 37° C. |
| 100 | 1.062 | 0.02 |
| 200 | 1.273 | 0.008 |
| Control | 0.102 | 0.020 |

As shown in Table 1, the storage stability of each of the reverse transcriptase solutions stored at 4° C. containing oligo $dT_{12\text{-}18}$·poly A and magnesium chloride is significantly improved, as compared to the storage stability of the reverse transcriptase solution not containing oligo $dT_{12\text{-}18}$·poly A and magnesium chloride. With respect to the reverse transcriptase solutions stored at 37° C., as is also apparent from Table 1, the storage stability of each of the reverse transcriptase solutions containing oligo $dT_{12\text{-}18}$·poly A and magnesium chloride in a concentration in the range of from 0.5 to 50 mM (that is, up to the magnesium chloride concentration of $1.2 \times 10^{11}$ molecules, per molecule of the reverse transcriptase) is significantly improved, as compared to the storage stability of the reverse transcriptase solution not containing oligo $dT_{12\text{-}18}$·poly A and magnesium chloride.

EXAMPLE 2

In six glass vials were individually prepared six different types of solutions which respectively contained trehalose (molecular formula: $C_{12}H_{22}O_{11} \cdot 2H_2O$; molecular weight: 378.3) (manufactured and sold by Sigma Chemical Company, USA) in concentrations of 0, 1, 5, 10, 20 and 40% by weight and each of which contained 0.1 M of HEPES (manufactured and sold by DOJINDO LABORATORIES, Japan; pH 7.8), 0.1% of Triton X-100 (manufactured and sold by Sigma Chemical Company, USA), 0.15% of bovine serum albumin (manufactured and sold by Sigma Chemical Company, USA), 1 mU/$\mu$l of HIV-1 reverse transcriptase (manufactured and sold by SEIKA-GAKU KOGYO CO., LTD., Japan) and 20 mM of magnesium chloride (manufactured and sold by WAKO PURE CHEMICAL INDUSTRIES LTD., Japan). Thus, there were obtained sample solutions. The thus obtained sample solutions were stored for 7 days at 4° C. After the storage, each of the sample solutions was individually diluted using 0.1% Triton X-100, so that each of the sample solutions contained 0.4 mU/ml of the reverse transcriptase, thereby obtaining test samples. The reverse transcriptase activity of each of the obtained test samples was evaluated in substantially the same manner as in Example 1.

On the other hand, a control solution was prepared in substantially the same manner as described above, except that magnesium chloride and trehalose were not added. Storage of the prepared control solution at 4° C., and dilution of the control solution with 0.1% Triton X-100 were performed in the same manner as described above, to thereby obtain a control test sample. The reverse transcriptase activity of the obtained control test sample was evaluated in substantially the same manner as in Example 1.

The results are shown in Table 2.

TABLE 2

| Concentration of trehalose (%) | Reverse Transcriptase Activity (Absorbance at 405 nm) 4° C. |
|---|---|
| 0 (Comparative example) | 1.10 |
| 1 | 1.359 |
| 5 | 1.442 |
| 10 | 1.492 |
| 20 | 1.538 |
| 40 | 1.241 |
| Control | 0.102 |

As shown in Table 2, the storage stability of each of the reverse transcriptase solutions containing magnesium chloride and trehalose is significantly improved, as compared to the storage stability of the reverse transcriptase solution not containing magnesium chloride and trehalose.

EXAMPLE 3

A solution containing 0.1 M of HEPES (manufactured and sold by DOJINDO LABORATORIES, Japan; pH 7.8), 0.1% of Triton X-100 (manufactured and sold by Sigma Chemical Company, USA), 0.15% of bovine serum albumin (manufactured and sold by Sigma Chemical Company, USA), 1 mU/μl of HIV-1 reverse transcriptase (manufactured and sold by SEIKAGAKU KOGYO CO., LTD., Japan), 40% by weight of trehalose (manufactured and sold by Sigma Chemical Company, USA), 20 μg/ml of oligo $dT_{12-18}$·poly A (manufactured and sold by Pharmacia Fine Chemicals AB, Sweden) and 20 mM of magnesium chloride (manufactured and sold by WAKO PURE CHEMICAL INDUSTRIES LTD., Japan) was prepared and dispensed in three (3) glass vials. Thus, there were obtained sample solutions. The thus obtained sample solutions were stored for 7 days at 4° C., 20° C. and 37° C., respectively. After the storage at the respective temperatures, each of the sample solutions was individually diluted using 0.1% Triton X-100, so that each of the sample solutions contained 0.4 mU/ml of the reverse transcriptase, thereby obtaining test samples. The reverse transcriptase activity of each of the obtained test samples was evaluated in substantially the same manner as in Example 1.

On the other hand, three control solutions were prepared in substantially the same manner as described above, except that trehalose, oligo $dT_{12-18}$·poly A and magnesium chloride were not added. Storage of the prepared three control solutions at the respective temperatures, and dilution of the control solutions with 0.1% Triton X-100 were performed in the same manner as described above, to obtain three control test samples. The reverse transcriptase activity of each of the obtained control test samples was evaluated in substantially the same manner as in Example 1.

The results are shown in Table 3.

TABLE 3

| | Reverse Transcriptase Activity (Absorbance at 405 nm) | | |
|---|---|---|---|
| | 4° C. | 20° C. | 37° C. |
| Example | 1.472 | 1.362 | 1.342 |
| Control | 0.102 | 0.054 | 0.020 |

As is apparent from Table 3, with respect to the reverse transcriptase solution containing a combination of oligo $dT_{12-18}$·poly A, trehalose and magnesium chloride, the stability thereof for the storage at a temperature up to at least 4° C. was confirmed.

EXAMPLE 4

A solution containing 0.1 M of HEPES (manufactured and sold by DOJINDO LABORATORIES, Japan; pH 7.8), 0.1% of Triton X-100 (manufactured and sold by Sigma Chemical Company, USA), 0.15% of bovine serum albumin (manufactured and sold by Sigma Chemical Company, USA), 1 mU/μl of HIV-1 reverse transcriptase (manufactured and sold by SEIKAGAKU KOGYO CO., INDUSTRIES LTD., Japan), 40% by weight of trehalose (manufactured and sold by Sigma Chemical Company, USA), 20 μg/ml of oligo $dT_{12-18}$·poly A (manufactured and sold by Pharmacia Fine Chemicals AB, Sweden) and 20 mM of magnesium chloride (manufactured and sold by WAKO PURE CHEMICAL INDUSTRIES LTD., Japan) was prepared and dispensed in seven (7) glass vials. Thus, there were obtained sample solutions. One of the thus obtained sample solutions, without being stored, was diluted using 0.1% Triton X-100, so that the sample solution contained 0.4 mU/ml of the reverse transcriptase, thereby obtaining a non-stored test sample. The reverse transcriptase activity of the obtained non-stored test sample was evaluated in substantially the same manner as in Example 1. The remaining sample solutions were stored at 4° C. for 2 months, 4 months, 6 months, 8 months, 10 months and 12 months, respectively. After the storage for the respective periods of time at 4° C., each of the stored sample solutions was individually diluted using 0.1% Triton X-100, so that each of the sample solutions contained 0.4 mU/ml of the reverse transcriptase, thereby obtaining test samples. The reverse transcriptase activity of each of the obtained test samples was evaluated in substantially the same manner as in Example 1.

On the other hand, seven control solutions were prepared in substantially the same manner as described above, except that trehalose, oligo $dT_{12-18}$·poly A and magnesium chloride were not added. Storage of the prepared seven control solutions for the above-mentioned respective periods of time at 4° C., and dilution of the control solutions with 0.1% Triton X-100 were performed in the same manner as described above, to obtain seven control test samples. The reverse transcriptase activity of each of the obtained seven control test samples was evaluated in substantially the same manner as in Example 1.

The results are shown in Table 4.

TABLE 4

| Storage Period of Time | Reverse Transcriptase Activity (Absorbance at 405 nm) | |
|---|---|---|
| | Example | Control |
| Non-stored | 1.528 | 1.605 |
| 2 months | 1.707 | 0.031 |
| 4 months | 1.654 | 0.018 |
| 6 months | 1.558 | 0.011 |
| 8 months | 1.659 | -0.011 |
| 10 months | 1.514 | 0.032 |
| 12 months | 1.556 | 0.003 |

As is apparent from Table 4, it was confirmed that the reverse transcriptase solution containing a combination of oligo $dT_{12-18}$·poly A, trehalose and magnesium chloride can be stably stored at 4° C. at least for one year.

EXAMPLE 5

In four glass vials were individually prepared four different types of solutions which respectively contained four different kinds of bivalent metal salts, namely, magnesium chloride (manufactured and sold by WAKO PURE CHEMICAL INDUSTRIES LTD., Japan), calcium chloride (manufactured and sold by WAKO PURE CHEMICAL INDUSTRIES LTD., Japan), manganese(II) chloride (manufactured and sold by WAKO PURE CHEMICAL Industries Ltd., Japan) and magnesium sulfate (manufactured and sold by WAKO PURE CHEMICAL Industries Ltd., Japan) individually in a concentration of 20 mM and each of which contained 0.1 M of HEPES (manufactured and sold by DOJINDO LABORATORIES, Japan; pH 7.8), 0.1% of Triton X-100 (manufactured and sold by Sigma Chemical Company, USA), 0.15% of bovine serum albumin (manufactured and sold by Sigma Chemical Company, USA), 1 mU/μl of HIV-1 reverse transcriptase (manufactured and sold by SEIKAGAKU KOGYO CO., LTD., Japan), 40% by weight of trehalose (manufactured and sold by Sigma Chemical Company, USA) and 20 μg/ml of oligo $dT_{12-18}$·poly A (manufactured and sold by Pharmacia Fine Chemicals AB, Sweden). Another set of four solutions of the same types as mentioned above was prepared in the same manner as described above. Thus, there were obtained two sets of sample solutions. The obtained two sets of sample solutions were stored for 7 days at 4° C. and at 20° C., respectively. After the storage at the respective temperatures, each of the sample solutions was individually diluted using 0.1% Triton X-100, so that each of the sample solutions contained 0.4 mU/ml of the reverse transcriptase, thereby obtaining test samples. The reverse transcriptase activity of each of the obtained test samples was evaluated in substantially the same manner as in Example 1.

On the other hand, two control solutions were prepared in substantially the same manner as described above, except that trehalose, oligo $dT_{12-18}$·poly A and a bivalent metal salt were not added. Storage of the prepared two control solutions at the respective temperatures, and dilution of the control solutions with 0.1% Triton X-100 were performed in the same manner as described above, to thereby obtain two control test samples. The reverse transcriptase activity of each of the obtained control test samples was evaluated in substantially the same manner as in Example 1.

The results are shown in Table 5.

TABLE 5

| Metal Salt | Reverse Transcriptase Activity (Absorbance at 405 nm) | |
| --- | --- | --- |
| | 4° C. | 20° C. |
| Magnesium Chloride | 1.433 | 1.326 |
| Calcium Chloride | 1.612 | 1.552 |
| Manganese (II) Chloride | 1.542 | 1.526 |
| Magnesium sulfate | 1.524 | 1.263 |
| Control | 0.080 | 0.039 |

As is apparent from Table 5, with respect to not only the reverse transcriptase solution containing oligo $dT_{12-18}$·poly A and trehalose and containing magnesium chloride but also the reverse transcriptase solutions individually containing oligo $dT_{12-18}$·poly A and trehalose and containing a bivalent metal salt other than magnesium chloride (such as calcium chloride, manganese(II) chloride or magnesium sulfate) instead of magnesium chloride, the stability thereof for the storage at a temperature up to at least 4° C. was confirmed.

EXAMPLE 6

In two glass vials were individually prepared two different types of solutions which respectively contained oligo $dT_{12-18}$·poly A (manufactured and sold by Pharmacia Fine Chemicals AB, Sweden) and oligo $dA_{12-18}$·poly U (manufactured and sold by Pharmacia Fine Chemicals AB, Sweden) in a concentration of 20 μg/ml and each of which contained 0.1 M of HEPES (manufactured and sold by DOJINDO LABORATORIES, Japan; pH 7.8), 0.1% of Triton X-100 (manufactured and sold by Sigma Chemical Company, USA), 0.15% of bovine serum albumin (manufactured and sold by Sigma Chemical Company, USA), 1 mU/μl of HIV-1 reverse transcriptase (manufactured and sold by SEIKAGAKU KOGYO CO., LTD., Japan), 40% by weight of trehalose (manufactured and sold by Sigma Chemical Company, USA) and 20 mM of magnesium chloride as a bivalent metal salt (manufactured and sold by WAKO PURE CHEMICAL INDUSTRIES LTD., Japan). Thus, there were obtained two different sample solutions. The thus obtained two different sample solutions were stored for 7 days at 4° C. After the storage, each of the sample solutions was individually diluted using 0.1% Triton X-100, so that each of the sample solutions contained 0.4 mU/ml of the reverse transcriptase, thereby obtaining two different test samples. The reverse transcriptase activity of each of the obtained test samples was evaluated in substantially the same manner as in Example 1.

On the other hand, a control solution was prepared in substantially the same manner as described above, except that none of trehalose, oligo $dT_{12-18}$·poly A, oligo $dT_{12-18}$·poly U and the bivalent metal salt were added. Storage of the prepared control solution, and dilution of the control solution with 0.1% Triton X-100 were performed in the same manner as described above, to thereby obtain a control test sample. The reverse transcriptase activity of the obtained control test sample was evaluated in substantially the same manner as in Example 1.

The results are shown in Table 6.

TABLE 6

| Combination of a template and a primer | Reverse Transcriptase Activity (Absorbance at 405 nm) 4° C. |
| --- | --- |
| oligo $dT_{12-18}$ · poly A | 1.555 |
| oligo $dA_{12-18}$ · poly U | 1.413 |
| Control | 0.112 |

As is apparent from Table 6, with respect to not only the reverse transcriptase solution containing a combination of oligo $dT_{12-18}$·poly A, trehalose and magnesium chloride but also the reverse transcriptase solution containing oligo $dA_{12-18}$·poly U (as a nucleic acid containing a transcriptional initiation site recognizable by the reverse transcriptase) instead of oligo $dT_{12-18}$·poly A, the storage stability thereof was confirmed.

EXAMPLE 7

A solution containing 0.1 M of HEPES (manufactured and sold by DOJINDO LABORATORIES, Japan; pH 7.8), 0.1% of Triton X-100 (manufactured and sold by Sigma Chemical Company, USA), 0.15% of bovine serum albumin (manufactured and sold by Sigma Chemical Company, USA), 1 mU/µl of HIV-1 reverse transcriptase (manufactured and sold by SEIKAGAKU KOGYO CO., LTD., Japan), 40% by weight of trehalose (manufactured and sold by Sigma Chemical Company, USA), 20 µg/ml of oligo $dT_{12-18}$·poly A (manufactured and sold by Pharmacia Fine Chemicals AB, Sweden) and 20 mM of magnesium chloride (manufactured and sold by WAKO PURE CHEMICAL INDUSTRIES LTD., Japan) was prepared. The thus prepared solution was dispensed by 0.5 ml in seven (7) glass vials. Using a freeze-drier, the dispensed solutions were freeze-dried. Thus, there were obtained freeze-dried samples. One of the obtained samples was dissolved in 0.5 ml of distilled water, and diluted using 0.1% Triton X-100 without being stored, so that the sample solution contained 0.4 mU/ml of the reverse transcriptase, thereby obtaining a non-stored test sample. The reverse transcriptase activity of the obtained non-stored test sample was evaluated in substantially the same manner as in Example 1. The remaining freeze-dried samples were stored for 2 months, 4 months, 6 months, 8 months, 10 months and 12 months, respectively. After the storage for the respective periods of time, each of the freeze-dried samples was individually dissolved in 0.5 ml of distilled water and diluted using 0.1% Triton X-100 were performed in the same manner as described above, so that each of the sample solutions contained 0.4 mU/ml of the reverse transcriptase, thereby obtaining test samples. The reverse transcriptase activity of each of the test samples was evaluated in substantially the same manner as mentioned above.

On the other hand, seven control freeze-dried samples were prepared in substantially the same manner as described above, except that oligo $dT_{12-18}$·poly A, trehalose and magnesium chloride were not added. Storage of the prepared seven control freeze-dried samples for the above-mentioned respective periods of time, dissolution of the control samples in 0.5 ml of distilled water, and dilution of the control samples with 0.1% Triton X-100 were performed in the same manner as described above, to thereby obtain seven control test samples. The reverse transcriptase activity of each of the obtained control test samples was evaluated in substantially the same manner as in Example 1.

The results are shown in Table 7.

TABLE 7

| Storage Period of Time | Reverse Transcriptase Activity (Absorbance at 405 nm) | |
|---|---|---|
| | Example | Control |
| Non-stored | 1.429 | 1.555 |
| 2 months | 1.707 | 1.431 |
| 4 months | 1.633 | 1.218 |
| 6 months | 1.658 | 1.111 |
| 8 months | 1.499 | 0.621 |
| 10 months | 1.586 | 0.419 |
| 12 months | 1.634 | 0.200 |

As is apparent from Table 7, it was confirmed that each of the freeze-dried samples prepared from the reverse transcriptase solutions containing a combination of oligo $dT_{12-18}$·poly A, trehalose and magnesium chloride can be stably stored at least for one year.

EXAMPLE 8

In three glass vials were individually prepared three different types of solutions which respectively contained an HIV-1 reverse transcriptase (manufactured and sold by SEIKAGAKU KOGYO CO., LTD., JAPAN) in concentrations of 10 U/µl, 1 mU/µl and 0.01 mU/µl and each of which contained 0.1 M of HEPES (manufactured and sold by DOJINDO LABORATORIES, Japan; pH 7.8), 0.1% of Triton X-100 (manufactured and sold by Sigma Chemical Company, USA), 0.15% of bovine serum albumin (manufactured and sold by Sigma Chemical Company, USA), 40% by weight of trehalose (manufactured and sold by Sigma Chemical Company, USA), 20 µg/ml of oligo $dT_{12-18}$·poly A (manufactured and sold by Pharmacia Fine Chemicals AB, Sweden) and 20 mM of magnesium chloride (manufactured and sold by WAKO PURE CHEMICAL INDUSTRIES LTD., Japan). Two other sets of solutions were prepared in the same manner as described above, with respect to two types of solutions respectively having HIV-1 reverse transcriptase concentrations of 10 U/µl and 1 mU/µl. Thus, one sample solution was obtained with respect to a solution having an HIV-1 reverse transcriptase concentration of 0.01 mU/µl; and three sets of sample solutions were obtained with respect to two types of solutions respectively having HIV-1 reverse transcriptase concentrations of 10 U/µl and 1 mU/µl. Each of the thus obtained three types of sample solutions was individually stored for 7 days at 4° C., at 20° C. and at 37° C. (With respect to the solution having HIV-1 reverse transcriptase in a concentration of 0.01 mU/µl, it was stored at 4° C. only.) After the storage at the respective temperatures, each of the sample solutions was individually diluted using 0.1% Triton X-100, so that each of the sample solutions contained 0.4 mU/ml of the reverse transcriptase, thereby obtaining test samples. The reverse transcriptase activity of each of the obtained test samples was evaluated in substantially the same manner as in Example 1.

On the other hand, three types of control solutions were prepared in substantially the same manner as described above, except that trehalose, oligo $dT_{12-18}$·poly A and magnesium chloride were not added. Storage of the prepared three types of control solutions at the respective temperatures, and dilution of the control solutions with 0.1% Triton X-100 were performed in the same manner as described above, to thereby obtain three types of control test samples. The reverse transcriptase activity of each of the obtained control test samples was evaluated in substantially the same manner as in Example 1.

With respect to solutions respectively having HIV-1 reverse transcriptase concentrations of 10 U/µl, 1 ml/µl and 0.01 mU/µl, the evaluation results are shown in Table 8, Table 9 and Table 10, respectively.

TABLE 8

[Solution having HIV reverse transcriptase concentration of 10 U/µl]

| | Reverse Transcriptase Activity (Absorbance at 405 nm) | | |
|---|---|---|---|
| | 4° C. | 20° C. | 37° C. |
| Example | 1.339 | 1.422 | 1.299 |
| Control | 0.002 | 0.059 | 0.039 |

TABLE 9

[Solution having HIV reverse transcriptase concentration of 1 mU/μl]

| | Reverse Transcriptase Activity (Absorbance at 405 nm) | | |
|---|---|---|---|
| | 4° C. | 20° C. | 37° C. |
| Example | 1.472 | 1.362 | 1.342 |
| Control | 0.102 | 0.054 | 0.020 |

TABLE 10

[Solution having HIV reverse transcriptase concentration of 0.01 mU/μl]

| | Reverse Transcriptase Activity (Absorbance at 405 nm) 4° C. |
|---|---|
| Example | 1.292 |
| Control | 0.153 |

As is apparent from Tables 8, 9 and 10, with respect to the reverse transcriptase solutions respectively having HIV-1 reverse transcriptase concentrations of 0.01 mU/μl, 1 mU/μl and 10 U/μl and containing a combination of trehalose, oligo $dT_{12-18}$·poly A and magnesium chloride, the stability thereof for the storage at a temperature up to at least 4° C. was confirmed.

REFERENCE EXAMPLE 1

In six glass vials were individually prepared six different types of solutions which respectively contained oligo $dT_{12-18}$·poly A (manufactured and sold by Pharmacia Fine Chemical AB, Sweden) in concentrations of 0, 0.2, 2, 20, 200 and 2000 μg/ml and each of which contained 0.1 M of HEPES (manufactured and sold by DOJINDO LABORATORIES, Japan; pH 7.8), 0.1% of Triton X-100 (manufactured and sold by Sigma Chemical Company, USA), 0.15% of bovine serum albumin (manufactured and sold by Sigma Chemical Company, USA), 1 mU/μl of HIV-1 reverse transcriptase (manufactured and sold by SEIKA-GAKU KOGYO CO., LTD., Japan) and 40% by weight of trehalose (manufactured and sold by Sigma Chemical Company, USA). Thus, there were obtained sample solutions. The thus obtained sample solutions were stored for 7 days at 4° C. After the storage, each of the sample solutions was individually diluted using 0.1% Triton X-100, so that each of the sample solutions contained 0.4 mU/ml of the reverse transcriptase, thereby obtaining test samples. The reverse transcriptase activity of each of the obtained test samples was evaluated in substantially the same manner as in Example 1.

On the other hand, a control solution was prepared in substantially the same manner as described above, except that oligo $dT_{12-18}$·poly A and trehalose were not added. Storage of the prepared control solution, and dilution of the control solution with 0.1% Triton X-100 were performed in the same manner as described above, to thereby obtain a control test sample. The reverse transcriptase activity of the obtained control test sample was evaluated in substantially the same manner as in Example 1.

The results are shown in Table 11.

TABLE 11

| Oligo $dT_{12-18}$ · poly A (μg/ml) | Reverse Transcriptase Activity (Absorbance at 405 nm) 4° C. |
|---|---|
| 0 (Comparative example) | 0.326 |
| 0.2 | 0.932 |
| 2 | 1.336 |
| 20 | 1.329 |
| 200 | 1.201 |
| 2000 | 0.741 |
| Control | 0.102 |

INDUSTRIAL APPLICABILITY

According to the present invention, there is provided a reverse transcriptase composition having improved storage stability, comprising a reverse transcriptase, an effective stabilizing amount of at least one organic stabilizing reagent selected from the group consisting of trehalose and a nucleic acid containing a transcriptional initiation site recognizable by the reverse transcriptase, and an effective stabilizing amount of a metal salt capable of producing bivalent positive ions in an aqueous solution of the metal salt. The reverse transcriptase composition of the present invention, which has improved storage stability, can be stably stored for a prolonged period of time at a temperature up to at least 4° C. without suffering denaturation of the reverse transcriptase, so that it becomes possible to achieve reduction in the energy and cost required in various techniques employing the reverse transcriptase. Further, by virtue of a relatively high temperature usable for stable storage, the viscosity of the reverse transcriptase composition of the present invention can be advantageously maintained at a low level, so that it becomes possible to accurately dispense the composition by a quantity corresponding to a desired enzyme activity, thereby achieving high reproducibility in experiments using the reverse transcriptase. Therefore, in a method generally employed for the determination of a virus, in which a reverse transcriptase activity is used as an index, the transcriptase composition of the present invention can be advantageously used as a standard substance for determining the amount of virus.

I claim:

1. A reverse transcriptase composition having improved storage stability, comprising a reverse transcriptase, an effective stabilizing amount of an organic stabilizing reagent comprised of a combination of trehalose and a nucleic acid consisting of a transcriptional initiation site recognizable by said reverse transcriptase, and an effective stabilizing amount of a metal salt capable of producing bivalent positive ions in an aqueous solution of said metal salt.

2. The reverse transcriptase composition according to claim 1, wherein said nucleic acid is at least one hybridization product selected from the group consisting of a hybridization product of a template RNA composed essentially of adenine ribonucleotide and a primer composed essentially of oligodeoxythymidine nucleotide, a hybridization product of a template RNA composed essentially of uracil ribonucleotide and a primer composed essentially of oligodeoxyadenosine nucleotide, and a hybridization product of a template RNA composed essentially of guanine ribonucleotide and a primer composed essentially of oligodeoxycytosine nucleotide.

3. The reverse transcriptase composition according to claim 1, wherein said metal salt is at least one member selected from the group consisting of magnesium chloride, calcium chloride, manganese (II) chloride and magnesium sulfate.

4. The reverse transcriptase composition according to claim 1, wherein said trehalose is contained in an amount of from 30 to $3.1 \times 10^{11}$ molecules, per molecule of said reverse transcriptase.

5. The reverse transcriptase composition according to claim 1, wherein said nucleic acid is contained in an amount of from 250 to $6 \times 10^{12}$ molecules, relative to $10^6$ molecules of said reverse transcriptase.

6. The reverse transcriptase composition according to claim 1, wherein said metal salt is contained in an amount of from 1 to $1.2 \times 10^{11}$ molecules, per molecule of said reverse transcriptase.

7. The reverse transcriptase composition according to claim 1, which is in the form of an aqueous solution.

8. The reverse transcriptase composition according to claim 1, which is in a freeze-dried form.

9. A method for improving storage stability of a reverse transcriptase, which comprises adding to a reverse transcriptase an effective stabilizing amount of at least one organic stabilizing reagent selected from the group consisting of trehalose and a nucleic acid containing a transcriptional initiation site recognizable by said reverse transcriptase, and an effective stabilizing amount of a metal salt capable of producing bivalent positive ions in an aqueous solution of said metal salt.

10. The method according to claim 9, wherein said at least one organic stabilizing reagent is a combination of trehalose and a nucleic acid consisting of a transcriptional initiation site recognizable by said reverse transcriptase.

11. The method according to claim 9, wherein said nucleic acid is at least one hybridization product selected from the group consisting of a hybridization product of a template RNA composed essentially of adenine ribonucleotide and a primer composed essentially of oligodeoxythymine nucleotide, a hybridization product of a template RNA composed essentially of uracil ribonucleotide and a primer composed essentially of oligodeoxyadenine nucleotide, and a hybridization product of a template RNA composed essentially of guanine ribonucleotide and a primer composed essentially of oligodeoxycytosine nucleotide.

12. The method according to claim 9, wherein said metal salt is at least one member selected from the group consisting of magnesium chloride, calcium chloride, manganese (II) chloride and magnesium sulfate.

13. The method according to claim 9, wherein said trehalose is added to said reverse transcriptase in an amount of from 30 to $3.1 \times 10^{11}$ molecules, per molecule of said reverse transcriptase.

14. The method according to claim 9, wherein said nucleic acid is added to said reverse transcriptase in an amount of from 250 to $6 \times 10^{12}$ molecules, relative to $10^6$ molecules of said reverse transcriptase.

15. The method according to claim 9, wherein said metal salt is added to said reverse transcriptase in an amount of from 1 to $1.2 \times 10^{11}$ molecules, per molecule of said reverse transcriptase.

16. The method according to claim 9, wherein each of said reverse transcriptase, said at least one organic stabilizing reagent and said metal salt is individually used in the form of an aqueous solution thereof, whereby a storage stability-improved, aqueous reverse transcriptase composition is obtained.

17. The method according to claim 16, which further comprises subjecting said storage stability-improved, aqueous reverse transcriptase composition to freeze-drying.

* * * * *